(12) United States Patent
Avnery (10) Patent No.: US 6,623,705 B2
(45) Date of Patent: Sep. 23, 2003

(54) GAS CONVERSION SYSTEM

(75) Inventor: Tzvi Avnery, Winchester, MA (US)

(73) Assignee: Advanced Electron Beams, Inc., Wilmington, MA (US)

( * ) Notice: Subject to any disclaimer, the term of this patent is extended or adjusted under 35 U.S.C. 154(b) by 0 days.

(21) Appl. No.: 09/883,853

(22) Filed: Jun. 18, 2001

(65) Prior Publication Data

US 2002/0005345 A1 Jan. 17, 2002

Related U.S. Application Data (60) Provisional application No. 60/214,577, filed on Jun. 28, 2000, and provisional application No. 60/213,358, filed on Jun. 20, 2000.

(51) Int. Cl.[7] .............................................. B01J 19/08
(52) U.S. Cl. ........................................ 422/186; 422/121
(58) Field of Search .................................. 422/186, 121

(56) References Cited

U.S. PATENT DOCUMENTS

| | | | |
|---|---|---|---|
| 3,761,065 A | * 9/1973 | Rich et al. ..................... 261/76 |
| 3,869,362 A | 3/1975 | Machi et al. ............. 204/157.1 |
| 4,167,466 A | * 9/1979 | Orr, Jr. et al. ............... 204/176 |
| 4,324,759 A | 4/1982 | Aoki et al. ..................... 422/62 |
| 4,752,450 A | 6/1988 | Dietrich et al. ............. 422/186 |
| 4,882,020 A | 11/1989 | Maezawa et al. ......... 204/157.3 |
| 4,915,916 A | 4/1990 | Ito et al. ....................... 422/186 |
| 4,969,984 A | 11/1990 | Kawamura et al. ....... 204/157.3 |
| 5,015,443 A | 5/1991 | Ito et al. ..................... 422/186 |
| 5,041,271 A | 8/1991 | Aoki et al. ................. 423/235 |
| 5,319,211 A | 6/1994 | Matthews et al. ........ 250/492.3 |
| 5,357,291 A | 10/1994 | Schonberg et al. ....... 250/492.3 |
| 5,378,898 A | 1/1995 | Schonberg et al. ....... 250/492.3 |
| 5,457,269 A | 10/1995 | Schonberg .................. 588/212 |
| 5,468,356 A | 11/1995 | Uhm ........................... 204/164 |
| 5,523,577 A | 6/1996 | Schonberg et al. ....... 250/492.3 |
| 5,539,212 A | 7/1996 | Matthews et al. ........ 250/492.3 |
| 5,582,807 A | 12/1996 | Liao et al. ................... 423/210 |
| 5,693,195 A | 12/1997 | Saito et al. ............. 204/157.44 |
| 5,700,311 A | 12/1997 | Spencer ........................ 95/236 |
| 5,744,811 A | 4/1998 | Schonberg et al. ....... 250/492.3 |
| 5,770,785 A | 6/1998 | Tamura et al. .............. 588/900 |
| 5,834,722 A | 11/1998 | Tokunaga et al. ......... 204/157.3 |
| 5,853,680 A | 12/1998 | Iijima et al. ................. 423/220 |
| 5,993,612 A | 11/1999 | Rostaing et al. .......... 204/158.2 |
| 6,077,488 A | 6/2000 | Jain et al. .................... 423/210 |
| 6,080,281 A | 6/2000 | Attia ......................... 204/157.3 |

FOREIGN PATENT DOCUMENTS

| | | |
|---|---|---|
| EP | 0 579 105 A1 | 1/1994 |
| GB | 2 173 779 A | 10/1986 |
| JP | 63302924 | 12/1988 |
| WO | WO 97/01386 | 1/1997 |

OTHER PUBLICATIONS

Tian, C., and Vidal, C.R., "Single to Quadruple Ionization of $CO_2$ Due to Electron Impact," *Phys. Rev. A*, 58(5): 3783–3795 (1998).

Darici, Y., et al., "Electron Beam Dissociation of CO and $CO_2$ on ZnS Thin Films," *J. Vac. Sci. Technol. A*, 17(3); 692–697 (1999).

* cited by examiner

*Primary Examiner*—Kishor Mayekar
(74) *Attorney, Agent, or Firm*—Hamilton, Brook, Smith & Reynolds, PC (57) ABSTRACT

A gas conversion system for removing carbon dioxide from gases includes a duct through which gases are circulated. The duct has a port for introducing a reaction agent into the duct to the gases. An electron beam emitter is positioned relative to the duct for directing an electron beam into the duct to cause components of the carbon dioxide and the reaction agent to react to remove carbon dioxide from the gases and release oxygen.

12 Claims, 8 Drawing Sheets

GAS CONVERSION SYSTEM

RELATED APPLICATIONS

This application claims the benefit of U.S. Provisional Application No. 60/213,358, filed on Jun. 20, 2000, and U.S. Provisional Application No. 60/214,577, filed on Jun. 28, 2000. The entire teachings of the above applications are incorporated herein by reference.

BACKGROUND

Air circulation systems in commercial aircraft circulate a mixture of fresh and recirculated air to the occupants. A certain amount of fresh air is required to maintain healthy oxygen and carbon dioxide gas levels for the occupants. Typically, sufficient fresh air cannot be drawn into aircraft at altitudes above 40,000 feet because the air is very thin. Consequently, this prevents commercial aircraft from flying at such altitudes. Flying at altitudes above 40,000 feet would be desirable for commercial aircraft because the thin air at those altitudes offers less wind resistance than at lower altitudes, and therefore allows the aircraft to fly in a more fuel efficient manner.

SUMMARY

The present invention provides a gas conversion or treatment system which may be employed to remove carbon dioxide from gases. The gas conversion system of the present invention includes a duct through which the gases are circulated. The duct has a port for introducing a reaction agent into the duct to the gases. An electron beam emitter is positioned relative to the duct for directing an electron beam into the duct and causing components of the carbon dioxide and reaction agent to react to remove carbon dioxide from the gases and release oxygen.

In preferred embodiments, the carbon dioxide is within air. An air circulator is included for circulating the air which can be circulated within an enclosed environment. A separator separates solids from the gases which are formed by reaction of the components of the carbon dioxide and the reaction agent. In one embodiment, the reaction agent is water. The present invention may be within, part of, or be an air circulation or recirculation system.

The present invention is also directed to a method of removing carbon dioxide from gases including introducing a reaction agent to the gases and treating the reaction agent and the gases with an electron beam. The electron beam causes components of the carbon dioxide and the reaction agent to react to remove carbon dioxide from the gases and release oxygen. The carbon dioxide can be removed from air within an air circulation or recirculation system.

The present invention is additionally directed to a gas conversion system for removing $NO_X$ and $SO_X$ (nitrogen and sulfur oxides) from gases and includes a duct through which the gases flow. The duct has a port for introducing a reaction agent into the duct to the gases. First and second electron beam emitters are mounted to the duct opposite from each other for directing opposed electron beams into the duct and causing components of the $NO_X$, $SO_X$ and reaction agent to react to remove $NO_X$ and $SO_X$ from the gases. In one embodiment, the reaction agent is ammonia.

The present invention is also directed to a treatment system for removing a compound and includes a duct through which gases flow. The compound is mixed with the gases. The duct has a port for introducing a reaction agent into the duct to the gases. First and second electron beam emitters are mounted to the duct opposite from each other for directing opposed electron beams into the duct and causing components of the compound and reaction agent to react to remove the compound from the gases.

The present invention is further directed to an electron beam treatment system including a duct through which a substance to be treated flows. First and second electron beam emitters are mounted to the duct opposite from each other for directing opposed electron beams into the duct to treat the substance.

The present invention is also directed to an electron beam treatment system including an electron beam emitter for generating an electron beam through an exit window. A reaction chamber is mounted to the electron beam emitter for receiving the electron beam from the electron beam emitter. The reaction chamber has a nozzle for directing a substance towards the exit window for treatment and an outlet adjacent to the nozzle for receiving the treated substance.

The present invention can be employed in air circulation or recirculation systems for removing carbon dioxide and releasing oxygen to eliminate the need for drawing in fresh air. As a result, the air can be circulated in an enclosed environment. Such enclosed environment air circulation systems can be installed within commercial aircraft to provide the passengers with breathable air that has healthy levels of carbon dioxide and oxygen, while at the same time allowing the aircraft to fly at altitudes significantly above 40,000 feet where the aircraft is more fuel efficient. In addition, an embodiment of the present invention can be employed for removing $NO_X$ and $SO_X$ from the exhaust of vehicles or factories to reduce pollution. Other embodiments may be employed for removing or destroying other compounds or substances.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
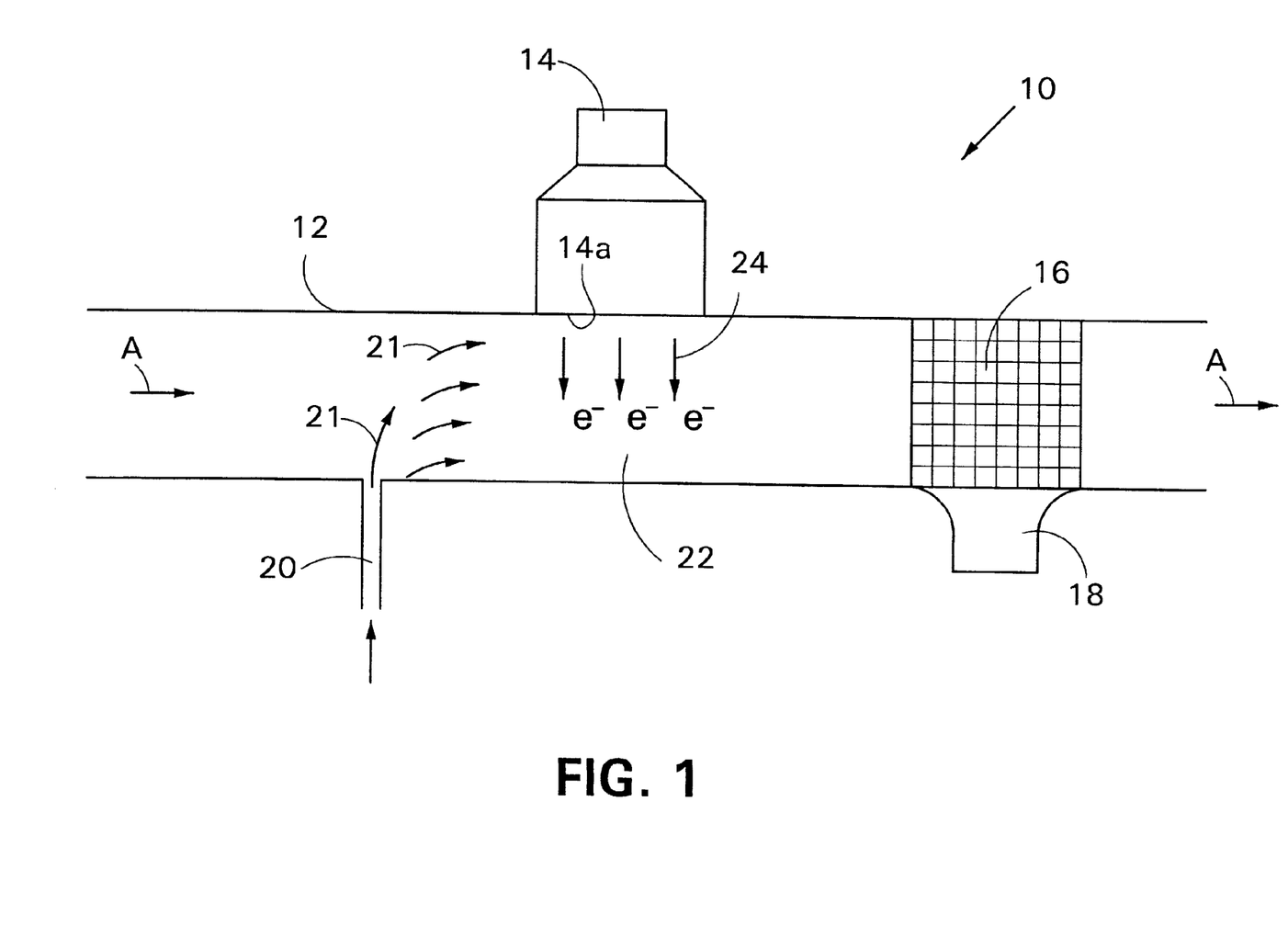
FIG. 1 is a side schematic view of an embodiment of the present invention gas conversion system.

Referring to FIG. 1, gas conversion or treatment system 10 is employed for removing carbon dioxide from gases and releasing oxygen. Often, gas conversion system 10 is included within or is part of an air circulation system for removing carbon dioxide from the air and releasing oxygen gas. Other common uses are removing carbon dioxide from and releasing oxygen into exhaust gases. Gas conversion system 10 includes a duct 12 through which gases flow or circulate in the direction of arrows A. Typically, a percentage of the gas or gases flowing through duct 12 is made up of carbon dioxide gas. A port 20 extending into duct 12 is employed for introducing a scavenging or reaction agent 21 into the duct 12 for mixing with the flowing gases. An electron beam emitter 14 is mounted to the duct 12 over an opening in the duct 12 in a sealed manner, typically downstream of port 20 for directing an electron beam 24 into the flowing gases within duct 12. The electron beam emitter 14 has an exit window 14a through which the electron beam 24 is directed. The electron beam emitter 14 is sized to cover virtually the entire cross section of duct 12 with electrons $e^-$ from the electron beam 24. This forms an irradiation zone 22 through which the flowing gases and reaction agent 21 pass. The electron beam 24 causes carbon dioxide gas to react with the reaction agent 21 to remove carbon dioxide from the flowing gases while at the same time releasing oxygen gas. Often, a byproduct results from the reaction and may be a solid. A separating device such as a filter 16 is typically positioned downstream of the electron beam emitter 14 and irradiation zone 22 for filtering these solids from the flowing gases. In addition, the filter 16 can be used in conjunction with a collector 18 for collecting the solids.

In use, the reaction agent 21 is continuously introduced into duct 12 while in a form that easily mixes with the flowing gases, such as in a gaseous or vapor form, mist, or fine powder. As the mixture of gases and reaction agent 21 pass through the irradiation zone 22, the electron beam 24 breaks apart carbon dioxide gas molecules ($CO_2$) into smaller components such as C, O or CO. The reaction agent 21 may also be broken up, depending upon the particular agent employed. Components of the carbon dioxide containing the element carbon react with components of the reaction agent 21, typically forming a solid, and are thereby removed from the flowing gas. Removing carbon bearing components from the flowing gas removes carbon dioxide gas therefrom.

In one embodiment, the reaction agent 21 is water ($H_2O$) which may be introduced into duct 12 through port 20 as a mist or vapor. The electron beam 24 breaks apart water molecules ($H_2O$) into smaller components such as H, OH or O, and carbon dioxide molecules ($CO_2$), as mentioned above. Once water ($H_2O$) and carbon dioxide molecules ($CO_2$) are broken up into smaller components, the components can react with each other. Carbon dioxide gas ($CO_2$) can react with water ($H_2O$) when irradiated by the electrons $e^-$ from the electron beam 24 as follows:

$$CO_2 + H_2O + \text{Electron Beam} \rightarrow (CH_2O)_n + O_2$$

The byproducts of the reaction can be a solid containing carbon components in the form of sugar, and oxygen gas. The solid containing the carbon elements is removed from the flowing gases while the released oxygen mixes with the gases. Consequently, the process removes carbon dioxide gases from the flowing gases and releases oxygen gas back into the gases. The released oxygen ($O_2$) is formed from oxygen components which do not become incorporated into the solid.

Some of the broken up carbon dioxide components might not have a chance to react with the components of the reaction agent 21 and might reform back into carbon dioxide gas. In one embodiment, this can be minimized by introducing a sufficient amount of the reaction agent 21 into duct 12 and causing sufficient mixing therein with the gases. In another embodiment, it might be desirable to maintain a certain level of carbon dioxide after passing irradiation zone 22 because too much oxygen could be a fire hazard. In such a case, a lesser amount of reaction agent 21 is needed. Once the solids formed from the reaction of the carbon dioxide with the reaction agent 21 are removed by filter 16, the treated or converted gases can be directed by duct 12 to the appropriate destination. In some embodiments, the treated gases are circulated within an enclosed environment, such as in air circulation systems, while in other embodiments, the treated gases are directed to the outside environment (atmosphere), such as in exhaust systems.

Duct 12 is commonly rectangular in cross section, but can also have any other suitable cross section such as polygonal, circular, or have a combination of curves and straight sides. A pump or blower can be used to inject the reaction agent 21 into duct 12 through port 20. Although gas conversion system 10 has been shown to have one port 20 for introducing the reaction agent into duct 12, alternatively, more than one port 20 can be employed. Additionally, a series of ports 20 can be positioned about duct 12 for introducing reaction agent 21 radially inwardly into duct 12. Electron beam emitter 14 is typically similar to those disclosed in U.S. patent application Ser. No. 09/349,592, filed Jul. 9, 1999 now U.S. Pat. No. 6,407,492 entitled "Electron Beam Accelerator," the entire contents of which are incorporated herein. Alternatively, other suitable electron beam emitters can be used. Filter 16 typically includes an electrostatic precipitator which increases the size of the particles of the solids and a mechanical filter downstream of the precipitator. Alternatively, filter 16 can consist of either the electrostatic precipitator or the mechanical filter. Collector 18 is often a collection container or bin for collecting solids under duct 12. Collector 18 can also include a conduit or chute for conveying the solids to a bin positioned apart from the duct 12. Gas conversion system 10 is often within or part of an air circulation system, including air conditioning and heating systems, but can also be a stand alone unit employed primarily for removing carbon dioxide from air and releasing oxygen. In such a case, an air circulator such as a fan or blower would be included for causing the air flow within duct 12. In embodiments where gas conversion system 10 is employed for treating exhaust gases, the gases are often the product of a combustion reaction and in many cases are able to flow through duct 12 without the aid of an air circulator.

A gas conversion system 10 for removing carbon dioxide from and adding oxygen to a breathable air supply flowing through duct 12 may be installed within an aircraft. This would allow the aircraft to have a closed air circulation system and eliminate the need for drawing in and circulating a percentage of fresh air. As previously mentioned, commercial aircraft typically fly no higher than about 40,000 feet because sufficient amounts of fresh air cannot be drawn into the aircraft at such altitudes. Gas conversion system 10 would allow an aircraft to fly at altitudes much higher than 40,000 feet since fresh air does not need to be drawn in. Flying at altitudes significantly higher than 40,000 feet is desirable because fuel consumption is lower and, therefore, the aircraft is more efficient. In addition to removing carbon dioxide and adding oxygen to breathable air, the electron beam 24 of gas conversion system 10 also kills airborne microorganisms passing through the electron beam 24. This reduces the possibility of spreading sickness on the aircraft since the air in the cabin is recirculated. Filter 16 may also be designed for filtering out ozone that is produced in the irradiation process. Such a design can include a reactive filter having a pellet bed of spherical manganese dioxide or platinum pellets.

Gas conversion system 10 may be employed for closed air circulation or recirculation systems in applications other than aircraft, such as buildings, motorized vehicles, water craft, space craft, etc. In addition, gas conversion system 10 may be employed for removing carbon dioxide gas from the exhaust of factories and motorized craft. Furthermore, reaction agents 21 other than water may be employed, such as lime. Also, gas conversion system 10 may be employed for removing carbon dioxide gas from ambient air, such as in large cities for improving the air quality. Multiple gas conversion systems 10 would typically be required to handle a large flow rate.

Figure 2:
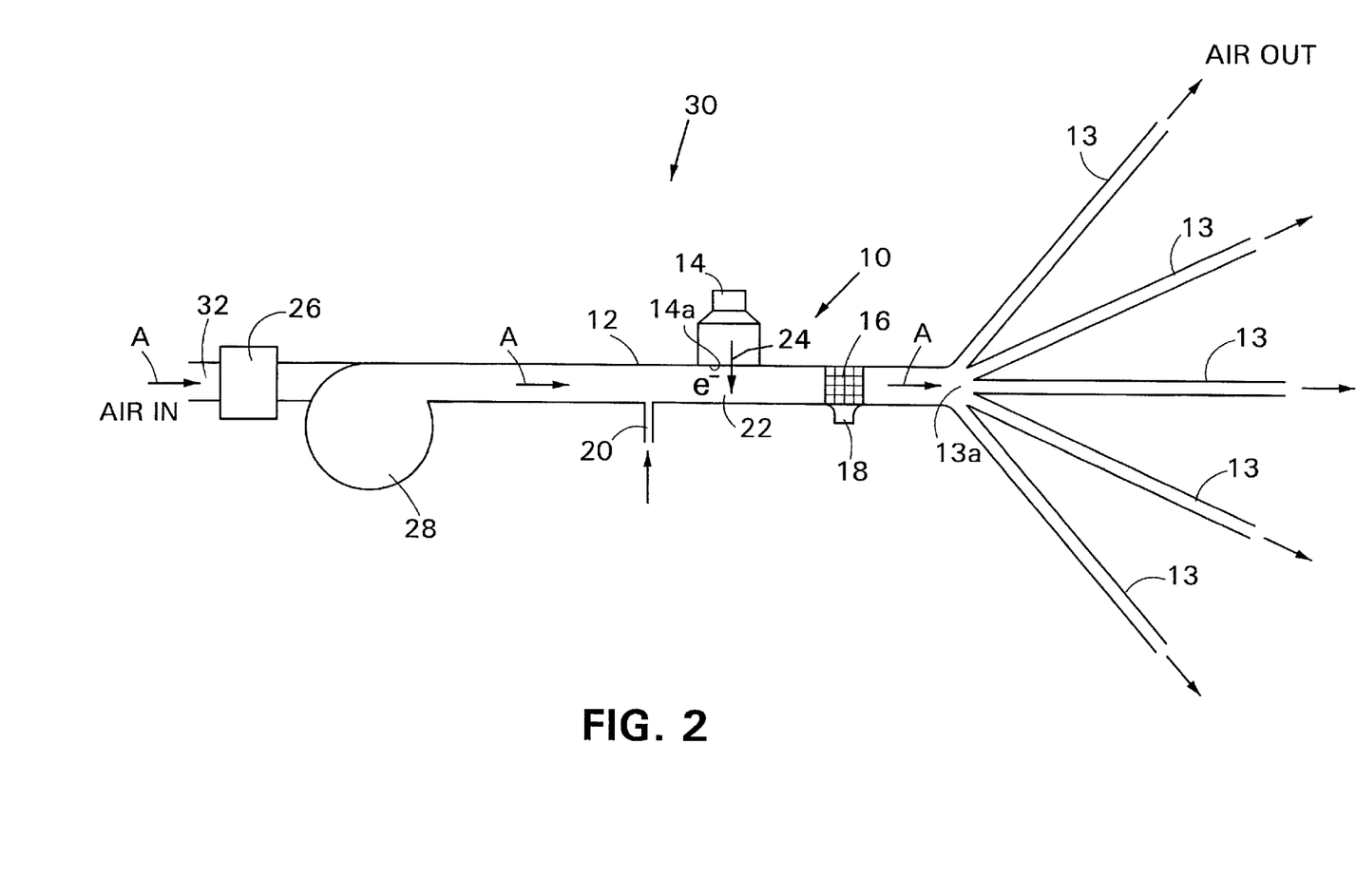
FIG. 2 is a schematic drawing of an air circulation system including the gas conversion system of FIG. 1.

FIG. 2 depicts an embodiment of gas conversion system 10 as part of an air circulation system 30. An air circulator 28 such as a fan or blower is positioned upstream of port 20 for causing air flow within duct 20. Air is provided to air circulator 28 through inlet 32 and passes through a filter 26 for filtering particles from the air. The air is treated by gas conversion system 10 in the manner previously discussed above. It is understood that air conditioning and/or heating components can also be included within air circulation system 30. Air circulation system 30 can eject air treated by gas conversion system 10 directly from duct 12. Optionally, a series of smaller ducts 13 can be connected to duct 12 at a junction 13a which deliver the treated air to different zones or areas. If air circulation system 30 is installed within an enclosed environment such as in the cabin of an aircraft, air ejected from ducts 13 would eventually reenter inlet 32 so that the air is circulated in a recirculating manner.

Figure 3:
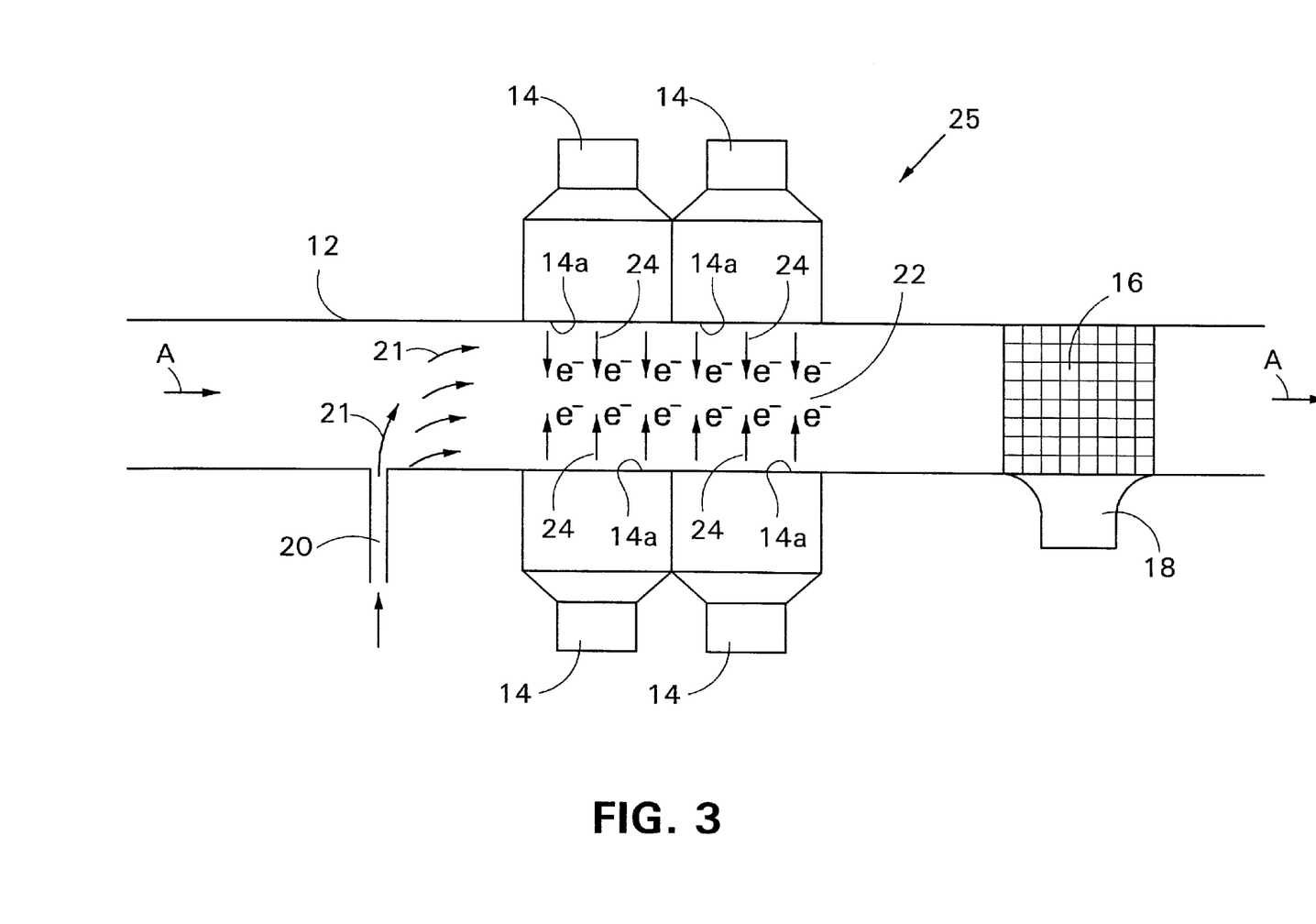
FIG. 3 is a side schematic view of another embodiment of the gas conversion system.
Figure 4:
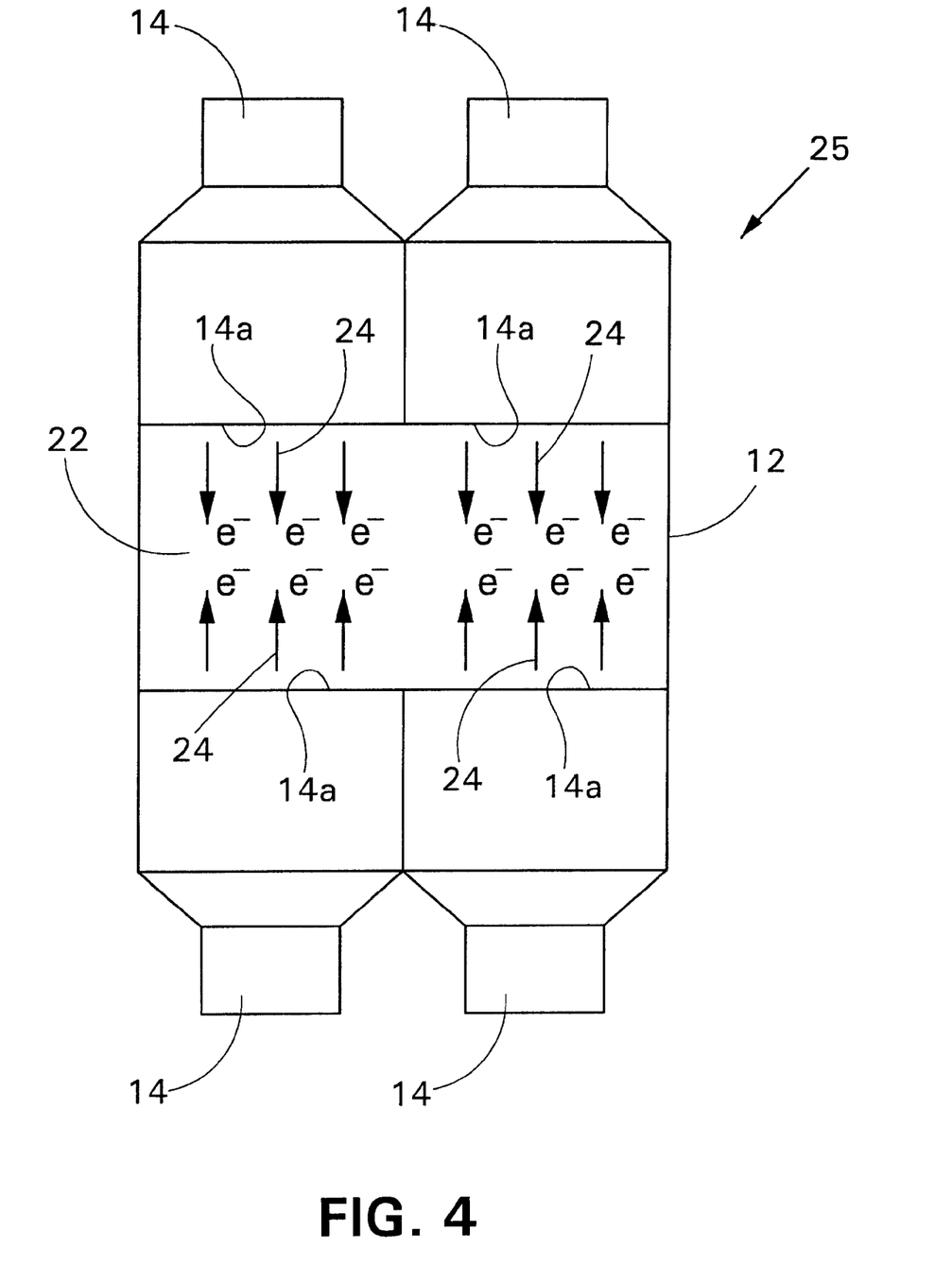
FIG. 4 is a cross sectional schematic view of the gas conversion system depicted in FIG. 3.

Referring to FIGS. 3 and 4, gas conversion or treatment system 25 can be used in applications similar to gas conversion system 10 but differs in that gas conversion system 25 includes multiple electron beam emitters 14. The electron beam emitters 14 are mounted to duct 12 in opposed axial alignment for directing electron beams 24 into irradiation zone 22 from opposite directions. This allows the height of duct 12 to be made greater than in gas conversion system 10. The electron beams 24 have a limited penetration depth into the flowing gases and reaction agent 21. The intensity of an electron beam 24 directed into gas decreases to zero very rapidly. Therefore, directing electron beams 24 from opposed directions enables the penetration depths of the opposed electron beams 24 to be combined to cover a cross section of greater height with more uniformity and better use of energy. As a result, a duct 12 having a relatively large height can be used while at the same time employing relatively low power electron beam emitters 14. For example, opposed electron beam emitters 14 operating at about 125 kV can be employed for irradiating a duct 12 that is about 5 inches high. In addition, the width of duct 12 can be increased by mounting electron beam emitters 14 side by side as depicted in FIG. 4. The electron beams 24 of side by side electron beam emitters 14 combine to provide continuous electron beam coverage across the width of duct 12. Furthermore, electron beam emitters 14 can be positioned in a manner where some of the electron beam emitters 14 are mounted to the duct 12 longitudinally along the duct 12 sequentially in the direction of gas flow resulting in upstream and downstream electron beam emitters 14. This allows higher air flow rates to be employed than with the single electron beam emitter 14 depicted in gas conversion system 10. Although a faster flow rate shortens the time that the gases and reaction agent 21 pass through an electron beam 24 of a given electron beam emitter 14, sequentially positioned electron beam emitters 14 provides an irradiation zone 22 of increased length to ensure that the gases and reaction agent 21 are irradiated for a sufficient amount of time to obtain the desired gas conversion reaction. In addition to sequentially positioning the electron beam emitters 14, electron beam emitters 14 can also be positioned on the sides of duct 12 to provide increased electron beam coverage.

The opposed electron beam emitter 14 configuration described for gas conversion system 25 can also be employed for removing nitrogen and sulfur oxide gases ($NO_X$ and $SO_X$) from exhaust or flue gases, for example from motorized vehicles or factories. Although a reaction agent 21 does not have to be employed, the use of ammonia ($NH_3$) as a reaction agent 21 is preferable for mixing with the gases within duct 12 before irradiation. The electron beams 24 break apart the $NO_X$, $SO_X$ and $NH_3$ molecules into smaller components and cause components of the $NO_X$, $SO_X$ and $NH_3$ to react resulting in the formation of ammonium sulfate and ammonium nitrate which is typically a solid in the form of dust. The dust can be separated from the flowing gases by a suitable filter arrangement 16 which can include an electrostatic precipitator to increase the size of the solid particles before filtering by a mechanical filter. Alternatively, the electrostatic precipitator or the mechanical filter can be used by itself. Consequently, $NO_X$ and $SO_X$ gases are removed from flowing gases by the present invention by the formation of solids containing nitrogen and sulfur components and the subsequent removal of the solids from the flowing gases. In some situations, only two opposed electron beam emitters 14 mounted to duct 12 may be required. Additionally, in other situations, electron beam emitters 14 can also be positioned side by side and/or in series along the direction of gas flow as depicted in FIGS. 3 and 4. Furthermore, some situations may require only a single electron beam emitter 14 such as in gas conversion system 10 (FIG. 1).

The present invention can be installed within the exhaust system of a motorized vehicle instead of a catalytic converter for removing $NO_X$ and $SO_X$ from the exhaust gases. The present invention can also be installed for removing $NO_X$ and $SO_X$ from the smokestacks of factories. In addition to removing $NO_X$ and $SO_X$ from gases, the opposed electron beam emitter 14 configuration can also be employed for destroying or removing volatile organic compounds (VOCs) from flowing gases. The VOCs can be in a gas, vapor or mist form when irradiated by electron beam emitters 14. The reaction agent 21 can be chosen for a particular organic compound.

Figure 5:
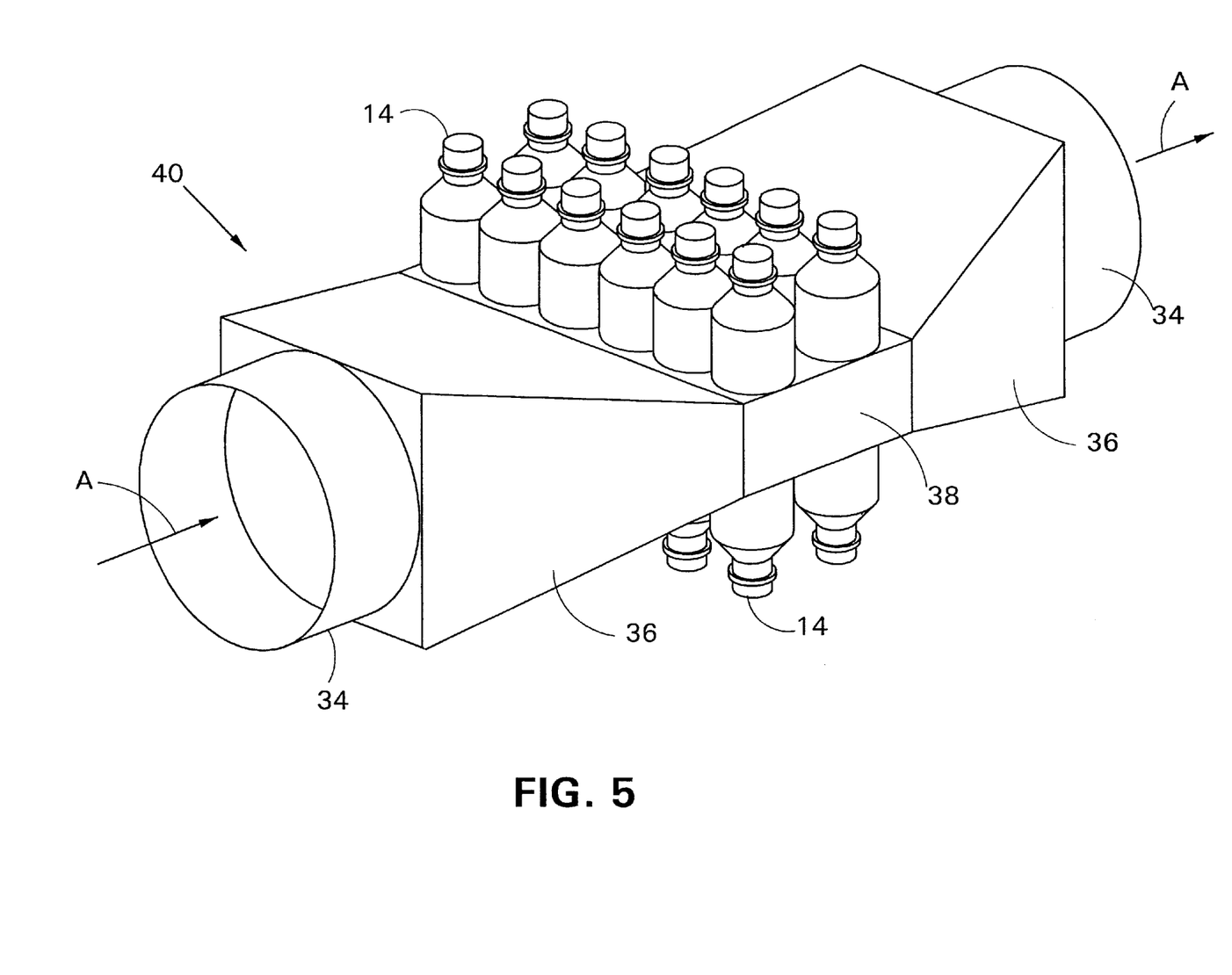
FIG. 5 is a perspective view of still another embodiment of the present invention.

Referring to FIG. 5, gas conversion or treatment system 40 is an embodiment of the present invention that can be employed for treating compounds or substances such as gases flowing through a circular conduit or duct 34. System 40 includes a rectangular duct portion 38 to which opposed electron beam emitters 14 are mounted. Typically, duct portion 38 has a lower height than duct 34, but is greater in width. This allows electron beam emitters 14 to be employed for sufficiently treating the substances flowing through duct 34 with electron beams 24 which ordinarily would not have a high enough power for penetrating deep enough through the flowing substances in duct 34 to obtain sufficient treatment. Transition portions 36 connect duct portion 38 to the duct 34 on opposite sides of duct portion 38. Transition portions 36 have a height that decreases moving from duct 34 to duct portion 38 and a width that increases moving from duct 34 to duct portion 38. Typically, transition portions 36 have angled top, bottom and side walls, but alternatively, the walls can be curved. The opposed electron beam emitters 14 are abutted in side by side relation in order to provide continuous electron beam coverage across the width of duct portion 38. One or more additional rows of electron beam emitters 14 can be positioned in the direction of flow to lengthen the time of irradiation, as shown. If the height of the duct portion 38 is low enough, a single unopposed row of electron beam emitters 14 can be employed. Although a port 28 and a separating device 16 are not depicted in FIG. 5, it is understood that such features can be included in system 40. System 40 can be employed for treatment the same substances as systems 10 and 25. In addition, the angled transition portions 36 can be employed when using two opposed electron beam emitters 14 or a single electron beam emitter 14.

Figure 6:
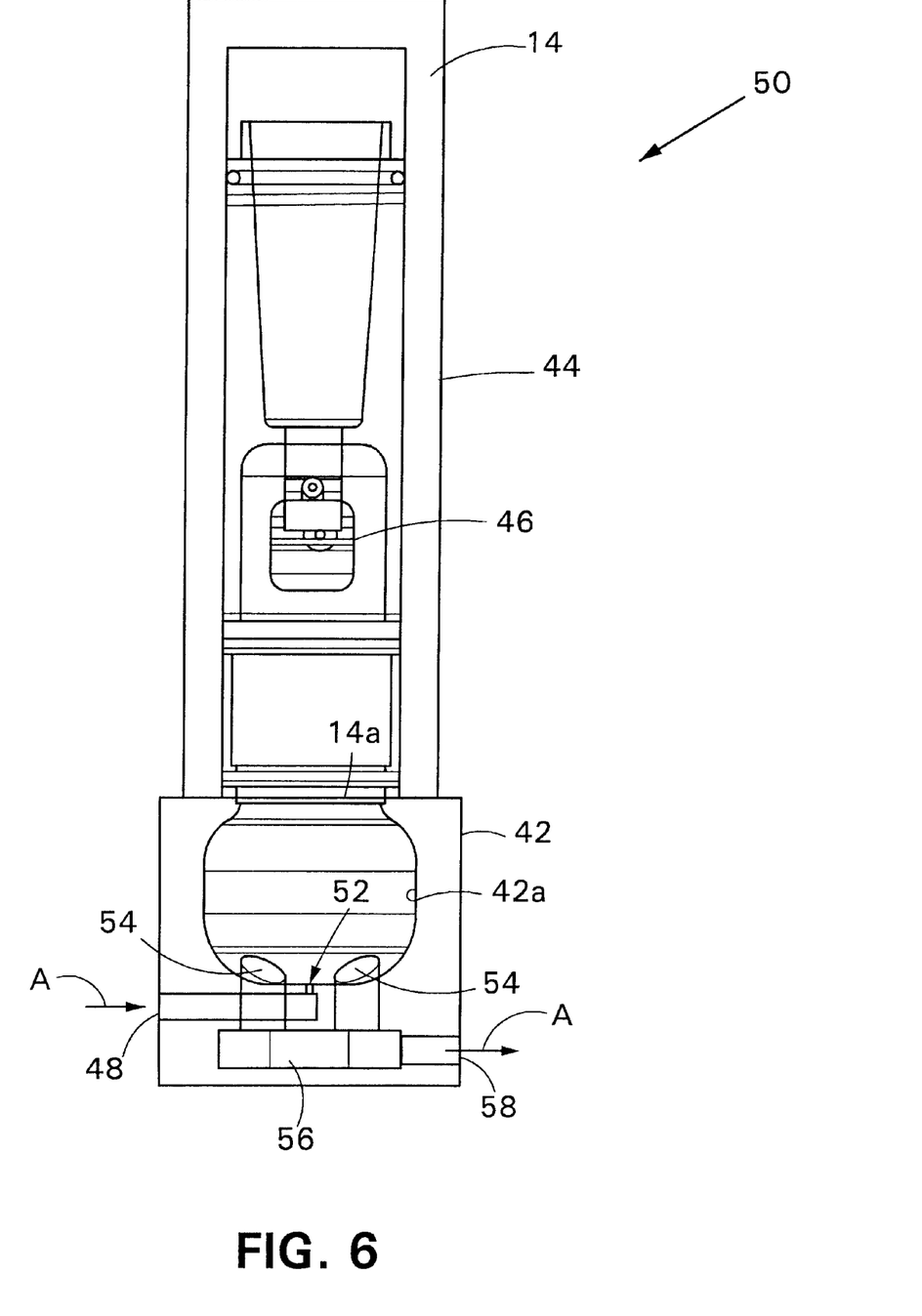
FIG. 6 is a schematic side sectional view of yet another embodiment of the present invention.
Figure 7:
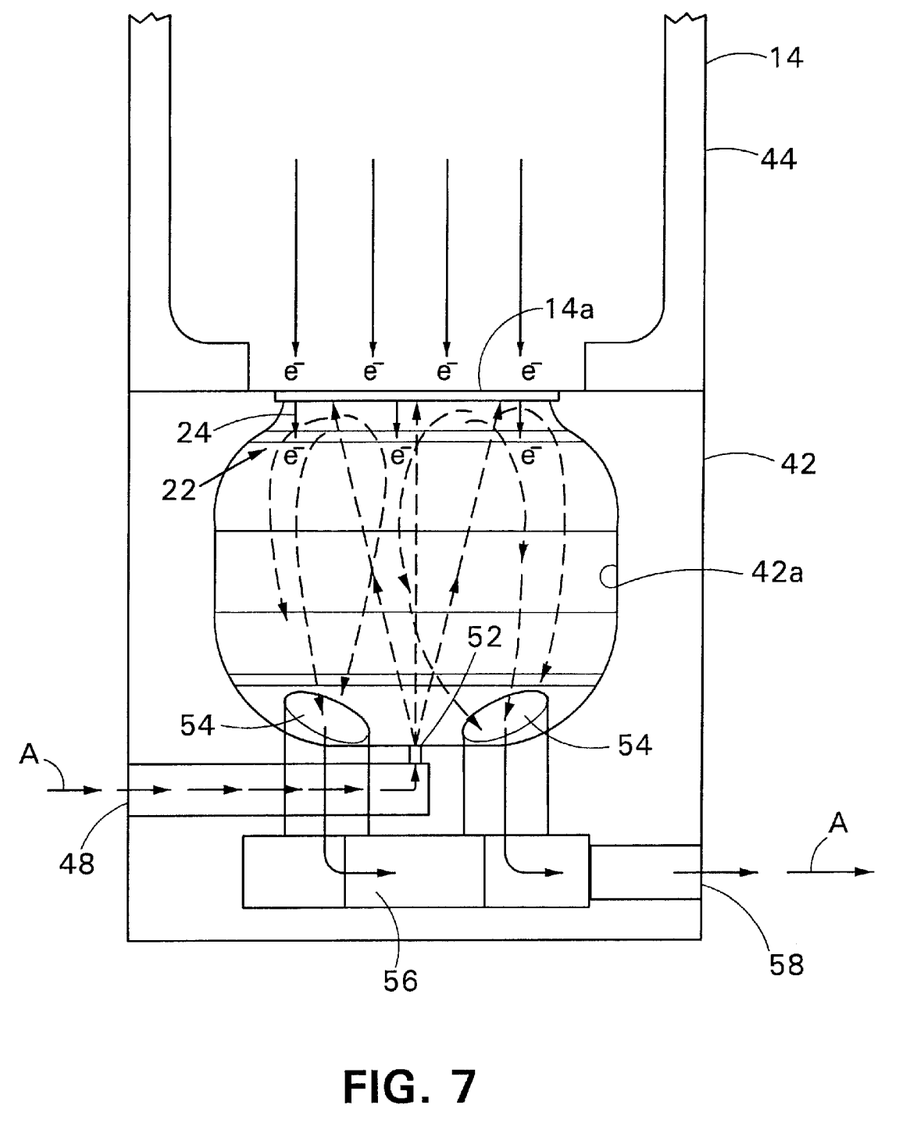
FIG. 7 is an enlargement of the bottom portion of FIG. 6.
Figure 8:
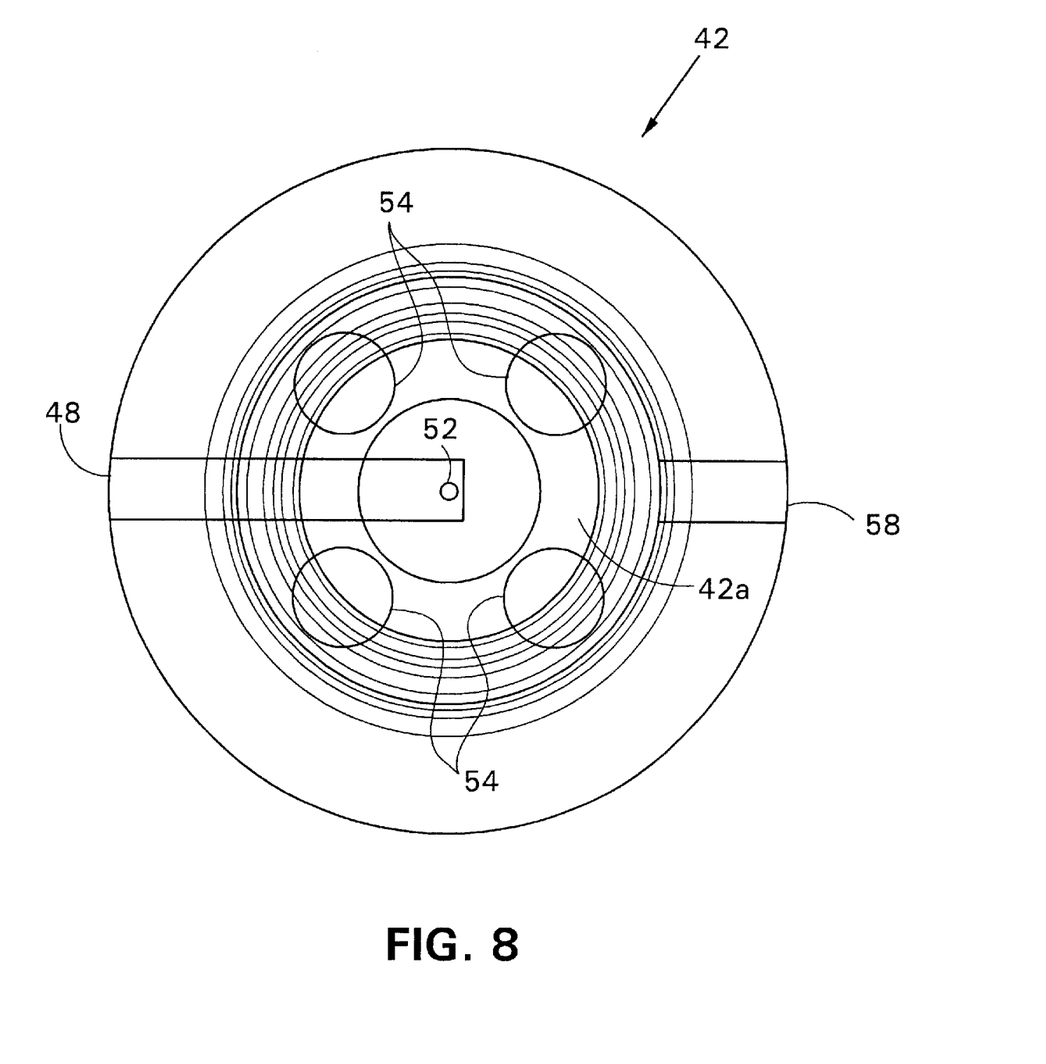
FIG. 8 is a top schematic view of the reaction chamber of FIG. 6.

Referring to FIGS. 6–8, gas conversion or treatment system 50 is yet another embodiment of the present invention which is suitable for treating relatively small flow rates of substances such as gases. System 50 is small or compact and is suitable for installation on the exhaust systems of motorized vehicles. System 50 includes a small low power electron beam emitter 14 that is mounted to a reaction chamber 42. Electron beam emitter 14 includes a cylindrical housing 44 having an exit window 14a at one end. An electron generator 46 positioned within the housing generates electrons e⁻ which are accelerated through exit window 14a in an electron beam 24. The distal end of the housing 44 of electron beam emitter 14 is mounted to reaction chamber 42 in a manner where the exit window 14a is positioned and sealed over the interior cavity 42a of reaction chamber 42 so that electrons e⁻ generated by electron generator 46 can be accelerated through exit window 14a into cavity 42a. Reaction chamber 42 has an inlet 48 through which flowing substances enter. A nozzle 52 (FIGS. 7 and 8) is positioned at or near the end of inlet 48 for directing a jet of the substances into the cavity 42a towards exit window 14a, the central axis of the jet being substantially perpendicular to exit window 14a and generally axially or along the same direction as electron beam 24. The nozzle 52 is centrally positioned at the bottom of cavity 42a opposite to exit window 14a for uniformly directing the substances towards exit window 14a. The intensity of the electron beam 24 into the flowing substances increases from close to zero at the bottom of cavity 42a to about full intensity adjacent exit window 14a. Consequently, the irradiation zone 22 in the area near exit window 14a has the highest intensity of electrons.

The substances are treated by the electron beam 24 in the irradiation zone 22 as it flows toward exit window 14a and then flows away from exit window 14a into a series of outlets 54 equally positioned about or around nozzle 52. This results in a mushroom shaped flow of substances. The cavity 42a forms a reverse flow duct in which the flow of substances is reversed. The substances are irradiated in both the forward and backward flow directions with the increasing and decreasing electron beam irradiation intensity resulting in relatively uniform irradiation. In one embodiment, four outlets 54 are employed. The outlets 54 are in communication with a chamber 56 which is connected to the outlet 58 of reaction chamber 42 through which the treated substances flow. In such an embodiment, electron beam emitter 14 can have a 2 inch diameter exit window 14a and operate at about 60 kV with reaction chamber 42 having a cavity 42a of about 2 inches in diameter by about 2 inches high.

If a reaction agent 21 is employed, the reaction agent 21 from a port 20 is typically mixed with the flowing substances before entering inlet 48. In addition, any separating or filter devices 16 would be positioned downstream from the outlet 58 of reaction chamber 42. System 50 can be employed for treating the same substances as systems 10, 25 and 40. In addition, system 50 can also be employed for sterilizing substances. Inlet 48, nozzle 52, cavity 42a, outlets 54, chamber 56 and outlet 58, including any connections to inlet 48 and outlet 58, can be considered to form a continuous duct.

While this invention has been particularly shown and described with references to preferred embodiments thereof, it will be understood by those skilled in the art that various changes in form and details may be made therein without departing from the scope of the invention encompassed by the appended claims.

For example, although gas conversion systems 10, 25, 40 and 50 are suitable for removing carbon dioxide, $NO_X$, $SO_X$ and VOCs from gases, alternatively, other gases, liquid substances or compounds may also be removed, treated, and/or sterilized. Particular reaction agents would be chosen to address the situation at hand. In some cases, it might be desirable not to introduce a reaction agent. Filters can be positioned upstream of the present invention systems for filtering out particles. The components that are removed from the gases or substances are usually in the form of a solid but in some cases can be a liquid. The filter 16 can be configured for trapping the liquid. In some cases, the liquid can be trapped without employing filter 16. The duct can also be configured for trapping solids without filter 16. Features of systems 10, 25, 40 and 50 as well as air circulation system 30 can be combined or omitted. Although ducts 12 and 34 have been depicted as straight and horizontally positioned, ducts 12 and 34 can have corners or bends and can be oriented vertically or at an angle, depending upon the situation at hand. For example, the ducts can have a zig zag configuration which provides shielding for X-rays. In addition, the shape and/or size of the cross section of ducts 12 and 34 can be varied along its length.

What is claimed is:

1. A gas conversion system for removing carbon dioxide from gases comprising:
   a duct through which the gases are circulated, the duct having a port for introducing a reaction agent into the duct to the gases;
   an electron beam emitter positioned relative to the duct for directing an electron beam into the duct and causing components of the carbon dioxide and the reaction agent to react to remove carbon dioxide from the gases and release oxygen; and
   a filter positioned within the duct downstream from the electron beam emitter for separating solids from the gases which are formed by reaction of the components of the carbon dioxide and the reaction agent.

2. The system of claim 1 in which the carbon dioxide is within air.

3. The system of claim 2 further comprising an air circulator for circulating the air.

4. The system of claim 3 in which the air is circulated within an enclosed environment.

5. The system of claim 1 in which the reaction agent is water.

6. The system of claim 1 further comprising a collector for collecting the solids.

7. An air treatment system for removing carbon dioxide from air comprising:
   an air circulator for circulating the air;
   a duct through which the air is circulated, the duct having a port for introducing a reaction agent into the duct to the air;

an electron beam emitter positioned relative to the duct for directing an electron beam into the duct and causing components of the carbon dioxide and the reaction agent to react to remove carbon dioxide from the air and release oxygen; and a filter positioned within the duct downstream from the electron beam emitter for separating solids from the gases which are formed by reaction of the components of the carbon dioxide and the reaction agent.

8. The system of claim 7 further comprising a collector for collecting the solids.

9. An air circulation system comprising:

a duct through which air is circulated, the duct having a port for introducing a reaction agent into the duct to the air;

an electron beam emitter positioned relative to the duct for directing an electron beam into the duct and causing components of the carbon dioxide and the reaction agent to react to remove carbon dioxide from the air and release oxygen; and a filter positioned within the duct downstream from the electron beam emitter for separating solids from the gases which are formed by reaction of the components of the carbon dioxide and the reaction agent.

10. The system of claim 9 further comprising a collector for collecting the solids.

11. An air treatment system for removing carbon dioxide from air in an enclosed environment comprising:

an inlet configured for providing the system with air from the enclosed environment;

an air circulator for circulating the air;

a duct through which the air is circulated, the duct having a port for introducing a reaction agent into the duct to the air; and an electron beam emitter positioned relative to the duct for directing an electron beam into the duct and causing components of the carbon dioxide and the reaction agent to react to remove carbon dioxide from the air and release oxygen, the duct being configured for ejecting treated air into the enclosed environment.

12. An air circulation system in an enclosed environment comprising:

an inlet configured for providing the system with air from the enclosed environment;

a duct through which the air is circulated, the duct having a port for introducing a reaction agent into the duct to the air; and an electron beam emitter positioned relative to the duct for directing an electron beam into the duct and causing components of the carbon dioxide and the reaction agent to react to remove carbon dioxide from the air and release oxygen, the duct being configured for ejecting treated air into the enclosed environment.

* * * * *